US011986524B1

(12) United States Patent
Peterson et al.

(10) Patent No.: US 11,986,524 B1
(45) Date of Patent: May 21, 2024

(54) METHODS FOR TREATMENT OF MENOPAUSAL SYMPTOMS

(71) Applicant: Next2Me, LLC, Oakland, CA (US)

(72) Inventors: Ralph L Peterson, Oakland, CA (US); Renee D Williman, Oakland, CA (US)

(73) Assignee: Next2Me, LLC, Oakland, CA (US)

( * ) Notice: Subject to any disclaimer, the term of this patent is extended or adjusted under 35 U.S.C. 154(b) by 0 days.

(21) Appl. No.: 18/418,822

(22) Filed: Jan. 22, 2024

Related U.S. Application Data

(63) Continuation-in-part of application No. 18/400,485, filed on Dec. 29, 2023, which is a continuation of application No. 18/111,702, filed on Feb. 20, 2023, now Pat. No. 11,857,626, which is a continuation-in-part of application No. 17/961,836, filed on Oct. 7, 2022, now Pat. No. 11,612,630, which is a continuation-in-part of application No. 17/732,639, filed on Apr. 29, 2022, now Pat. No. 11,529,383, which is a continuation-in-part of application No. 16/116,539, filed on Aug. 29, 2018, now abandoned, which is a continuation-in-part of application No. 14/223,392, filed on Mar. 24, 2014, now abandoned.

(60) Provisional application No. 61/936,116, filed on Feb. 5, 2014.

(51) Int. Cl.
| | |
|---|---|
| *A61K 41/00* | (2020.01) |
| *A61K 31/197* | (2006.01) |
| *A61K 31/4188* | (2006.01) |
| *A61K 31/4415* | (2006.01) |
| *A61K 31/455* | (2006.01) |
| *A61K 31/51* | (2006.01) |
| *A61K 31/519* | (2006.01) |
| *A61K 31/525* | (2006.01) |
| *A61K 31/661* | (2006.01) |
| *A61K 31/714* | (2006.01) |
| *A61K 36/06* | (2006.01) |
| *A61K 36/23* | (2006.01) |
| *A61K 36/68* | (2006.01) |
| *A61K 36/9068* | (2006.01) |

(52) U.S. Cl.
CPC ........ *A61K 41/0004* (2013.01); *A61K 31/197* (2013.01); *A61K 31/4188* (2013.01); *A61K 31/4415* (2013.01); *A61K 31/455* (2013.01); *A61K 31/51* (2013.01); *A61K 31/519* (2013.01); *A61K 31/525* (2013.01); *A61K 31/661* (2013.01); *A61K 31/714* (2013.01); *A61K 36/06* (2013.01); *A61K 36/23* (2013.01); *A61K 36/68* (2013.01); *A61K 36/9068* (2013.01)

(58) Field of Classification Search
CPC .................................................. A61K 41/0004
See application file for complete search history.

(56) References Cited

U.S. PATENT DOCUMENTS

2016/0346339 A1 * 12/2016 Finley .................. A61K 36/185

FOREIGN PATENT DOCUMENTS

CA         2609821 A1 * 11/2006   ........... A61K 9/0056

OTHER PUBLICATIONS

Pershin et al. Harmonic Oscillations of the Concentration of H-Bonds in Liquid Water; Laser Spectroscopy, vol. 16, No. 8, pp. 1184-1190 (Year: 2006).*

Ghazanfarpour et al. The Efficacy of Iranian Herbal Medicines in Alleviating Hot Flashes: A Systematic Review; International Journal of Reproductive Biomedicine, vol. 14, No. 3, pp. 155-166. (Year: 2016).*

* cited by examiner

*Primary Examiner* — Jeanette M Lieb
*Assistant Examiner* — Paul C Martin
(74) *Attorney, Agent, or Firm* — Francis Law Group

(57) ABSTRACT

Biochemical scaffolds for treating menopausal symptoms. The biochemical scaffolds include a base liquid medium, a bioenergetic platform and a vibrational platform. The bioenergetic platform includes at least one Krebs cycle modulator and/or neurotransmitter modulator and/or nuclear hormone receptor modulator. The vibrational platform includes at least one energy signature component, e.g., an herb. The biochemical scaffold is subjected to sequential harmonic oscillation for a defined, predetermined period of time, wherein the energy signature of the energy signature component is imparted to, captured, replicated, and retained by the liquid medium, and, when the biochemical scaffolds are delivered to and, thus, in communication with biological tissue, the biochemical scaffolds induce specific biochemical activities via the resonant transfer of the retained energy signature to the biological tissue and, hence, endogenous cells thereof.

5 Claims, 5 Drawing Sheets

--Prior Art--

N2M BIOCHEMICAL SCAFFOLDS

| Modulator | Physiological Action/Reaction | Element/Compound |
|---|---|---|
| Krebs Cycle Modulator | 1) Induce and/or modulate at least one Krebs cycle metabolic reaction, process and/or pathway<br><br>2) Induce production of $CO_2$, acetyl-CoA, $FADH_2$ and adenosine triphosphate (ATP) | ashwaganda, eleuthero root (or extract), maca, an amino acid, e.g., L-arginine and L-citrulline, and vitamins $B_2, B_1, B_3, B_5,$ and $B_9$ |
| Glutathione Modualator | 1) Induce the generation and/or proliferation of glutathione and/or a member of the glutathione family and, thereby, conversion of hydrogen peroxide to $H_2O$ and $O_2$<br><br>2) Induce the synthesis of catalase, i.e. an antioxidant | schisandra chinensis berry, damiana and epimedium and vitamine $B_2$<br><br>maca, nettles leaves, Fe and Cu, and vitamins $B_2, B_5, B_6$ and $B_7$ |
| Neurotransmitter Modulator | Induce the generation of electrochemical signals, i.e., neurotransmitters, and/or modulate the transmission thereof by and between neurons and, hence, cells | cannabidiol (DBD), epimedium, nettle leaf, maca, eleuthero root, Yohimbe, and vitamins $B_1$ and $B_6$ |

*FIG. 4A*

N2M BIOCHEMICAL SCAFFOLDS

| Modulator | Physiological Action/Reaction | Element/Compound |
|---|---|---|
| DNA Modulator | Support and/or enhance mitochondrial DNA activity | vitamin B$_{12}$ |
| Endocannabinoid System Modulator | Induce cell receptor activity; particularly, cannabinoid receptor activity | cannabidiol (CBD) |

*FIG. 4B*

METHODS FOR TREATMENT OF MENOPAUSAL SYMPTOMS

CROSS-REFERENCES TO RELATED APPLICATIONS

This application is a continuation-in-part of U.S. application Ser. No. 18/400,485, filed on Dec. 29, 2023, which is a continuation of U.S. application Ser. No. 18/111,702, filed on Feb. 20, 2023, now U.S. Pat. No. 11,857,626, which is a continuation-in-part of U.S. application Ser. No. 17/961,836, filed on Oct. 7, 2022, now U.S. Pat. No. 11,612,630, which is a continuation-in-part of U.S. application Ser. No. 17/732,639, filed on Apr. 29, 2022, now U.S. Pat. No. 11,529,383, which is a continuation-in-part of U.S. application Ser. No. 16/116,539, filed on Aug. 29, 2018, now abandoned, which is a continuation-in-part of U.S. application Ser. No. 14/223,392, now abandoned, filed on Mar. 24, 2014, which claims the benefit of U.S. Provisional Application No. 61/936,116, filed on Feb. 5, 2014.

FIELD OF THE INVENTION

The present invention relates to compositions and methods for inducing cell activity. More particularly, the present invention relates to biochemical scaffolds and associated methods for inducing, supporting and/or enhancing cell activity to treat menopausal symptoms.

BACKGROUND OF THE INVENTION

As is well known in the art, menopause generally comprises a loss of function of the ovaries after the cessation of normal ovulation cycles, which eventually affects all biological women. Menopause typically occurs naturally in middle age between the age of approximately 45 to 55. Menopause can, however, occur at an earlier age due to medical conditions or when induced through surgical removal of the ovaries.

As is also well known in the art, menopause is characterized by a significant decrease in production of estradiol by the ovaries and, hence, a significant decrease in plasma estradiol levels in biological women. This decrease in estradiol production induces a shift in hormone balance in the body, which often gives rise to a variety of symptoms associated with menopause.

Perimenopause, which is also referred to as pre-menopause or the climacteric, is a period prior to menopause when normal ovulation cycles gradually result in cessation of menses. As the ovulatory cycles lengthen and become more irregular, an individual's level of estradiol may initially increase, but will markedly drop upon the onset of menopause. Menopausal symptoms are thus often associated with a significant drop in estradiol levels.

Symptoms of perimenopause and menopause typically include physical symptoms, such as hot flashes and sweating associated with vasomotor instability. Additionally, psychological and emotional symptoms are also presented in individuals experiencing perimenopause and menopause, such as fatigue, irritability, insomnia, inability to concentrate, depression, memory loss, headache, anxiety, and nervousness. Further symptoms also include intermittent dizziness, paresthesia, palpitations, tachycardia, nausea, constipation, diarrhea, arthralgia, myalgia, cold hands and feet, weight gain, urinary incontinence, vaginal dryness, loss of pelvic muscle tone, increased risk of cardiovascular disease, and menopausal osteoporosis.

One of the most prevalent physiological menopausal symptoms is a hot flash. Hot flashes are often characterized by dysfunction in thermoregulation (i.e., vasomotor instability), which are typically associated with endocrine-associated hypersensitivity of the hypothalamus; more specifically, the hypothalamic preoptic area (POA). During a hot flash, the hypersensitive hypothalamus induces systemic vascular dilation that permits increased blood flow through blood vessels and, thereby, rapidly elevates body temperature to uncomfortable levels.

Hot flashes often occur at night and can, and often will, interfere with sleep and affect mental health, and, thereby, provide a lower quality of life.

Hot flashes are also associated with an increased risk of chronic diseases and disorders, such as obesity, metabolic syndrome, insulin resistance, non-alcoholic fatty liver, cardiovascular disease, and osteoporosis.

Various compositions and methods have thus been developed to treat menopausal symptoms; more specifically, hot flashes. One such method comprises hormone replacement therapy (HRT), which is a form of hormonal treatment that supplements naturally occurring hormones in the body.

Since women experiencing menopausal symptoms; particularly, hot flashes, typically present with increased levels of luteinizing hormone (LH) and follicle stimulating hormone (FSH), and decreased levels of estrogen and progestin, HRT treatments often include supplementation with estrogen and progestin to restore endogenous hormones to pre-menopausal levels.

There are, however, numerous disadvantages and drawbacks associated with HRT treatments. A major drawback associated with HRT treatments is a significantly increased risk of developing a multitude of diseases and disorders therefrom, including reproductive cancers, heart attack, and strokes.

Various non-hormonal compositions and methods have thus also been developed to treat menopausal symptoms. One seminal non-hormonal composition comprises fezolinetant (Veozah®). Fezolinetant is a neurokinin-3 (NK3) receptor antagonist developed by Astellas Pharma US, Inc., which reduces the occurrence of hot flashes by restoring vasomotor stability.

There are, however, similarly numerous disadvantages and drawbacks associated with administration of fezolinetant. A major drawback associated with administration of fezolinetant is a high risk of significant side effects, including abdominal disorders and pain associated therewith, diarrhea, insomnia, back pain, and elevated hepatic transaminases.

Although the noted compositions and methods have garnered some success in treating menopausal symptoms; particularly, hot flashes, there still remains a need for compositions, i.e., biochemical scaffolds, which more effectively and consistently address menopausal symptoms, and particularly, hot flashes, without the side effects and health risks associated with hormonal and non-hormonal compositions and methods.

It would thus be desirable to provide improved compositions (referred to herein as "biochemical scaffolds") and methods associated therewith that substantially reduce and, in most instances, abate the frequency and intensity of hot flashes associated with perimenopause and menopause without the side effects and health risks associated with hormonal and non-hormonal compositions and methods.

It is therefore an object of the present invention to provide biochemical scaffolds and methods associated therewith, which substantially abate the frequency and intensity of hot flashes associated with perimenopause and menopause without the side effects and health risks associated with hormonal and non-hormonal compositions and methods.

It is another object of the present invention to provide biochemical scaffolds and methods associated therewith that substantially abate the frequency and intensity of hot flashes associated with perimenopause and menopause by inducing and/or modulating a plurality of seminal molecular and cell activities.

SUMMARY OF THE INVENTION

The present invention is directed to biochemical scaffolds and associated methods, which substantially reduce the occurrence of hot flashes associated with perimenopause and menopause by inducing and/or modulating a plurality of molecular and cell activities.

In some embodiments of the invention, there are thus provided methods for reducing the occurrence of hot flashes associated with perimenopause and menopause comprising the steps of:
 (a) providing a biochemical scaffold comprising (i) a liquid medium, (ii) at least one Krebs cycle modulator that is adapted to induce and/or modulate at least one Krebs cycle metabolic reaction, process, and/or pathway, (iii) at least one neurotransmitter modulator adapted to induce and/or modulate generation of neurotransmitters and modulate the transmission thereof by and between neurons, (iv) at least one nuclear hormone receptor modulator adapted to induce and/or modulate nuclear hormone receptor activity, (v) at least one glutathione modulator adapted to induce catalase synthesis, (vi) at least one DNA modulator adapted to induce and/or modulate mitochondrial DNA activity, and (vii) at least one endocannabinoid system modulator adapted to induce and/or modulate endocannabinoid system activity;
 (b) subjecting the biochemical scaffold to harmonic oscillation; and
 (c) delivering a therapeutically effective amount of the biochemical scaffold to the subject.

In a preferred embodiment of the invention, the liquid medium comprises glycerin-based water.

In a preferred embodiment, the biochemical scaffold comprises a plurality of Krebs cycle modulators.

In a preferred embodiment, the plurality of Krebs cycle modulators comprises vitamin $B_1$, vitamin $B_2$, vitamin $B_3$, vitamin $B_5$, and vitamin $B_9$.

In a preferred embodiment, the biochemical scaffold also comprises a plurality of neurotransmitter modulators.

In a preferred embodiment, the plurality of neurotransmitter modulators comprises valerian root (*Valeriana officinalis* L.), sage (*Salvia officinalis*), and vitamin $B_6$.

In a preferred embodiment, the biochemical scaffold also comprises a plurality of nuclear hormone receptor modulators.

In a preferred embodiment, the plurality of nuclear hormone receptor modulators comprises black cohosh (*Actaea racemosa* L./*Cimicifuga racemosa* (L.) Nutt.), chasteberry (*Vitex agnus-castus* L.), red clover (*Trifolium pretense* L.), primrose (*Oenothera biennis*), fenugreek (*Trigonella foenum-graecum*), licorice root (*Glycyrrhiza glabra*), and dong quai (*Angelica sinensis*).

In a preferred embodiment, the glutathione modulator comprises vitamin $B_7$.

In a preferred embodiment, the DNA modulator comprises vitamin $B_{12}$.

In a preferred embodiment, the endocannabinoid system modulator comprises cannabidiol (CBD).

In some embodiments, the harmonic oscillation of the biochemical scaffold comprises a harmonic oscillation frequency in the range of approximately 0.0001 kHz to approximately 40000.0 kHz for a period of time in the range of at least 3.0 minutes to 60.0 minutes.

In a preferred embodiment, the harmonic oscillation comprises sequential harmonic oscillation comprising (i) a first frequency in the range of approximately 0.1 kHz to approximately 5.0 kHz for a first period of time in the range of 30.0 seconds to 3.0 minutes, (ii) a second frequency in the range of approximately 10.0 kHz to approximately 50.0 kHz for a second period of time in the range of 30.0 seconds to 3.0 minutes, (iii) a third frequency in the range of approximately 20.0 kHz to approximately 40.0 kHz for a third period of time in the range of 30.0 seconds to 3.0 minutes, (iv) a fourth frequency in the range of approximately 500.0 kHz to approximately 1000.0 kHz for a fourth period of time in the range of 30.0 seconds to 3.0 minutes, and (v) a fifth frequency in the range of approximately 20.0 kHz to approximately 50.0 kHz for a fifth period of time in the range of 30.0 seconds to 3.0 minutes.

In a preferred embodiment, when the biochemical scaffold is subjected to harmonic oscillation of the invention, retained energy signatures of one or more of the above referenced biochemical scaffold formulation components are transferred to the liquid medium, wherein, when the biochemical scaffold is delivered to biological tissue, the biochemical scaffolds further enhance the molecular and cellular activities induced by the Krebs cycle modulators, neurotransmitter modulators, nuclear hormone receptor modulators, glutathione modulator, DNA modulator and endocannabinoid system modulator through the resonant transfer of the retained energy signatures to the biological tissue and, hence, endogenous cells thereof.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which:

FIGS. 4A and 4B are tables of biochemical scaffolds, according to the invention.

DETAILED DESCRIPTION OF THE PREFERRED EMBODIMENT

Figure 1:
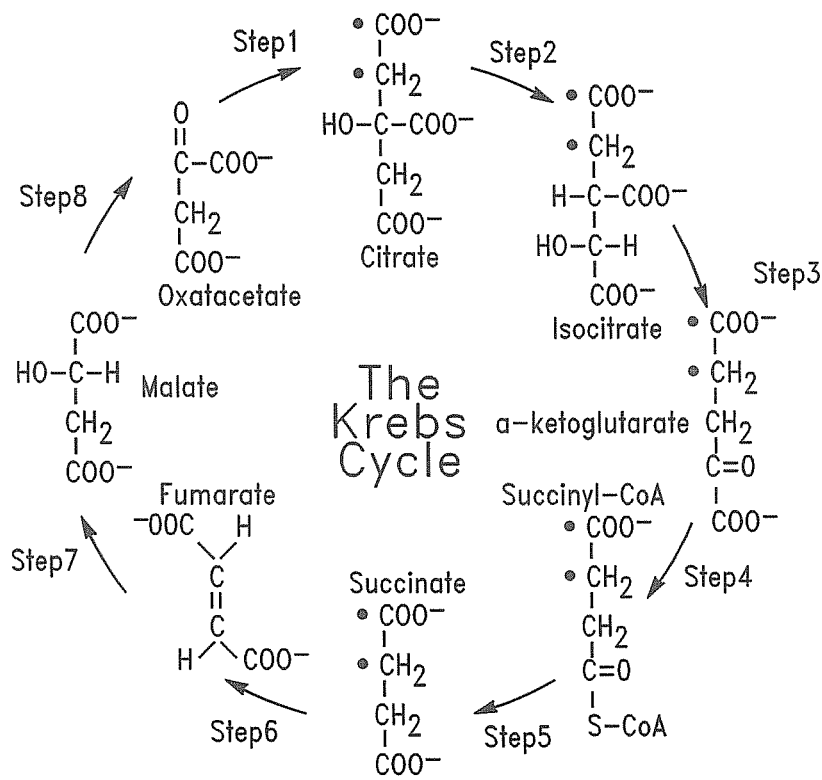
FIG. 1 is a schematic illustration of a Krebs cycle.
Figure 2:
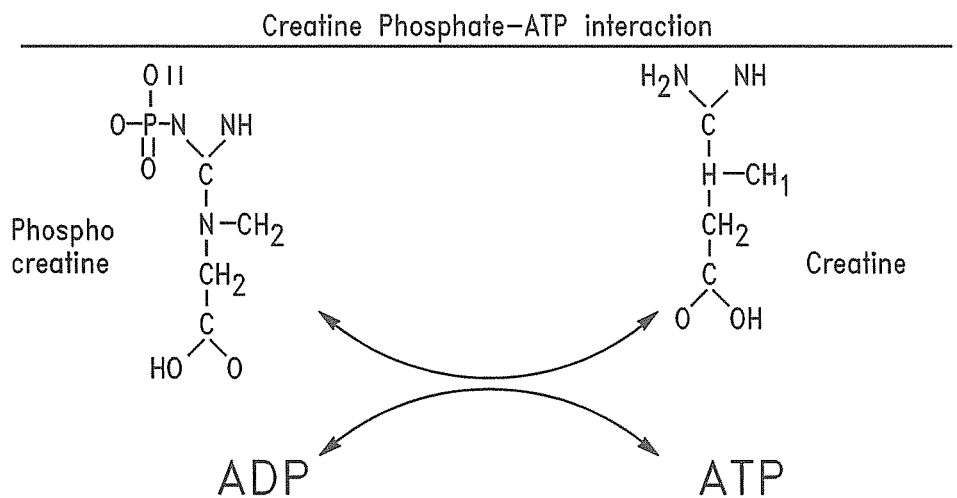
FIG. 2 is a schematic illustration of a creatine phosphate—ATP interaction.

Before describing the present invention in detail, it is to be understood that this invention is not limited to particularly exemplified formulations or methods as such may, of course, vary. Thus, although a number of formulations and methods similar or equivalent to those described herein can be used in the practice of the present invention, the preferred formulations and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

Finally, as used in this specification and the appended claims, the singular forms "a", "an" and "the" include plural referents unless the content clearly dictates otherwise.

Definitions

The terms "glycerin" and "glycerin-based water" are used interchangeably herein, and mean and include a solution comprising water (i.e., $H_2O$) and glycerol.

The term "structured water," as used herein, means and includes $H_2O$ comprising a hydrogen bond angle greater than 110°, more preferably, a hydrogen bond angle in the range of approximately 113° to 115°. According to the invention, the term "structured water" also means and includes $H_2O$ that is processed according to at least one of the methods disclosed in U.S. application Ser. No. 16/559,986, which is incorporated by reference herein.

The term "vibrational energy platform," as used herein, means and includes biologically targeted complex, stable, and efficient energetic blanks and glycerol water-soluble molecules, which, when programmed with a laser charged imprint of herbs, minerals, vitamins, amino acids, or pharmaceutical properties (creating energy-signature templates), help stimulate/enable/enhance vital cellular biochemical processes necessary to maintain homeostasis.

The term "biochemical agent" as used herein, means and includes any element, agent, drug, compound, composition of matter or mixture thereof comprising an energy signature component.

The terms "energy signature" and "energy signature component," are used interchangeably herein, mean and include the specific energetic or electromagnetic identity of a selective herb or biochemical agent and, hence, molecular structure(s) thereof when the herb or biochemical agent is exposed to radiation energy, such as radiation energy generated via harmonic oscillation.

The terms "energy signature" and "energy signature component," as used interchangeably herein, also mean and include the properties and functions of an herb or biochemical agent associated with the energetic identity of the herb or biochemical agent.

The term "Krebs cycle modulator," as used herein, means and includes an element, agent, drug, compound, composition of matter or mixture thereof, including its formulation, which induces and/or modulates a Krebs cycle metabolic reaction, process and/or pathway, including, without limitation, Krebs cycle product inhibition and/or substrate availability. According to the invention, suitable Krebs cycle modulators can comprise, without limitation, eleuthero root (or extract), maca, an amino acid, e.g., L-arginine and L-citrulline, and vitamins $B_1$, $B_2$, $B_3$, $B_5$, and $B_9$.

The term "neurotransmitter modulator," as used herein, means and includes an element, agent, drug, compound, composition of matter or mixture thereof, including its formulation, which induces the generation or proliferation of at least one neurotransmitter and/or modulates the transmission thereof by and between neurons and, hence, cells.

According to the invention, suitable neurotransmitter modulators comprise, without limitation, epimedium, stinging nettle leaf (also referred to herein as "stinging nettle"), maca root, eleuthero root, ginger root, yohimbe, vitamin $B_1$, vitamin $B_6$, valerian root (*Valeriana officinalis* L.), sage (*Salvia officinalis*), vitamin E, and phosphatidylserine.

The term "glutathione modulator," as used herein, means and includes an element, agent, drug, compound, composition of matter or mixture thereof, including its formulation, which induces the generation or proliferation of glutathione and/or the glutathione family, including, without limitation, glutathione peroxidase.

The term "glutathione modulator" also means and includes an element, agent, drug, compound, composition of matter or mixture thereof, including its formulation, which induces catalase synthesis.

According to the invention, suitable glutathione modulators comprise, without limitation, herbs, including, without limitation, *Schisandra chinensis* berry, damiana, epimedium, maca, and stinging nettle leaf; metal ions including iron (Fe) and copper (Cu); and B-vitamins selected from the group comprising vitamins $B_2$, $B_5$, $B_6$, and $B_7$.

The term "DNA modulator," as used herein, means and includes an element, agent, drug, compound, composition of matter or mixture thereof, including its formulation, that induces and/or modulates mitochondrial DNA, including protecting and/or facilitating the repair of mitochondrial DNA. According to the invention, a suitable DNA modulator comprises vitamin $B_{12}$.

The term "endocannabinoid system modulator," as used herein, means and includes an element, agent, drug, compound, composition of matter or mixture thereof, including its formulation, which induces and/or modulates cell receptor activity; particularly, cannabinoid receptor activity, i.e., the activity of CB1 or CB2. According to the invention, a suitable endocannabinoid system modulator comprises, without limitation, cannabidiol (CBD).

The term "nuclear hormone receptor modulator," as used herein, means and includes an element, agent, drug, compound, composition of matter or mixture thereof, including its formulation, which induces and/or modulates cell receptor activity; particularly, nuclear hormone receptor activity, e.g., the activity of estrogen receptor-α (ERα), estrogen receptor-β (ERβ), androgen receptor (AR), and mineralocorticoid receptor (MR).

According to the invention, suitable nuclear hormone receptor modulators comprise, without limitation, black cohosh (*Actaea racemosa* L./*Cimicifuga racemosa* (L.) Nutt.), chasteberry (*Vitex agnus-castus* L.), red clover (*Trifolium pretense* L.), primrose (*Oenothera biennis*), fenugreek (*Trigonella foenum-graecum*), licorice root (*Glycyrrhiza glabra*), dong quai (also referred to herein as "female ginseng" and *Angelica sinensis*), and red Korean ginseng (*Panax ginseng*).

The terms "cellular dysfunction" and "cell dysfunction" are used interchangeably herein and mean and include a reduction or impairment in physical structure or function of a cell.

The term "organ dysfunction", as used herein, means and includes a reduction or impairment in physical structure or function of a mammalian organ, including, without limitation, the cardiovascular vascular system (heart and lungs), digestive system (salivary glands, esophagus, stomach, liver, gallbladder, pancreas, intestines, colon, rectum, and anus), endocrine system (hypothalamus, pituitary gland, pineal body, thyroid, parathyroids, and adrenals), excretory system (kidneys, ureters, bladder, and urethra), immune system (lymphatic system, tonsils, adenoids, thymus, and spleen), integumentary system (skin, hair and nails), muscular system, nervous system (brain and spinal cord), reproductive system (ovaries, fallopian tubes, uterus, vagina, mammary glands, prostate, and penis), respiratory system (pharynx, larynx, trachea, bronchi, and diaphragm) and the skeletal system (bones, cartilage, ligaments, and tendons).

The terms "prevent" and "preventing" are used interchangeably herein, and mean and include reducing the frequency or severity of a disease, condition, dysfunction or disorder. The term does not require an absolute preclusion of the disease, condition, dysfunction, or disorder. Rather, this term includes decreasing the chance for disease occurrence.

The terms "treat" and "treatment" are used interchangeably herein, and mean and include medical management of a patient with the intent to cure, ameliorate, stabilize, or prevent a disease, pathological condition, dysfunction or disorder. The terms include "active treatment", i.e., treatment directed specifically toward the improvement of a disease, pathological condition, dysfunction, or disorder, and "causal treatment", i.e., treatment directed toward removal of the cause of the associated disease, pathological condition, dysfunction, or disorder.

The terms "treat" and "treatment" further include "palliative treatment", i.e., treatment designed for the relief of symptoms rather than the curing of the disease, pathological condition, dysfunction, or disorder, "preventative treatment", i.e., treatment directed to minimizing or partially or completely inhibiting the development of the associated disease, pathological condition, dysfunction, or disorder, and "supportive treatment", i.e., treatment employed to supplement another specific therapy directed toward the improvement of the associated disease, pathological condition, dysfunction, or disorder.

The term "substantially reduce" as used herein in conjunction with treating symptoms of perimenopause and menopause; particularly, hot flashes, means and includes reducing the frequency or intensity of the symptom(s).

The terms "pharmacological agent," "active agent" and "drug" are used interchangeably herein, and mean and include an agent, drug, compound, composition of matter or mixture thereof, including its formulation, which provides some therapeutic, often beneficial, effect. This includes any physiologically or pharmacologically active substance that produces a localized or systemic effect or effects in animals, including warm blooded mammals, humans, and primates; avians; domestic household or farm animals, such as cats, dogs, sheep, goats, cattle, horses and pigs; laboratory animals, such as mice, rats and guinea pigs; fish; reptiles; zoo and wild animals; and the like.

The terms "pharmacological agent," "active agent" and "drug" thus mean and include, without limitation, antibiotics, anti-viral agents, analgesics, steroidal anti-inflammatories, non-steroidal anti-inflammatories, anti-neoplastics, anti-spasmodics, modulators of cell-extracellular matrix interactions, proteins, hormones, enzymes and enzyme inhibitors, anticoagulants, antithrombotic agents, DNA, RNA, modified DNA, RNA, NSAIDs; inhibitors of DNA, RNA, or protein synthesis; compounds modulating cell migration, polypeptides, oligonucleotides, polynucleotides, nucleoproteins, and vasodilating agents.

The term "therapeutically effective", as used herein, means that the amount of a Krebs cycle modulator, glutathione modulator, neurotransmitter modulator, endocannabinoid system modulator, nuclear hormone receptor modulator, or DNA modulator, and/or biochemical scaffold formed therefrom, or pharmacological or bioactive agent administered to a subject is of sufficient quantity to ameliorate one or more causes, symptoms, or sequelae of a disease or disorder. Such amelioration only requires a reduction or alteration, not necessarily elimination, of the cause, symptom, or sequelae of a disease or disorder.

The terms "delivery" and "administration" are used interchangeably herein, and mean and include providing a Krebs cycle modulator, glutathione modulator, neurotransmitter modulator, endocannabinoid system modulator, nuclear hormone receptor modulator, or DNA modulator, and/or biochemical scaffold formed therefrom to a subject through any method appropriate to deliver formulations and/or scaffolds to a subject. Non-limiting examples of delivery methods include oral, sublingual, nasal, direct injection, topical application, etc.

The terms "patient" and "subject" are used interchangeably herein, and mean and include warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The term "comprise" and variations of the term, such as "comprising" and "comprises," means "including, but not limited to" and is not intended to exclude, for example, other additives, components, integers or steps.

The following disclosure is provided to further explain in an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

As indicated above, the present invention is directed to biochemical scaffolds and associated methods, which substantially reduce the occurrence and intensity of hot flashes associated with perimenopause and menopause by inducing and/or modulating at least one, more preferably, a plurality of molecular and cellular activities, including, without limitation, (i) at least one Krebs cycle metabolic reaction, process and/or pathway, (ii) generation or proliferation of glutathione and/or a member of the glutathione family and, thereby, induced catalase synthesis, (iii) generation or proliferation of at least one neurotransmitter, and/or modulating the transmission of at least one neurotransmitter by and between neurons, (iv) cell receptor activity, preferably, nuclear hormone receptor activity, and (v) mitochondrial DNA activity.

In a preferred embodiment of the invention, the biochemical scaffolds comprise two platforms (and components associated therewith): a vibrational energy platform and a bioenergetic platform.

In some embodiments of the invention, the bioenergetic platforms further comprise a liquid medium.

According to the invention, the biochemical scaffold can comprise any suitable medium, such as glycerol water solution (also referred to herein as "glycerin-based water") and distilled water. In some embodiments, the liquid medium comprises oxygen enriched glycerin infused water molecules.

In some embodiments of the invention, the liquid medium comprises structured water. As indicated above, structured water comprises $H_2O$ comprising a hydrogen bond angle greater than 110.0°, more preferably, a hydrogen bond angle in the range of approximately 113.0° to approximately 115.0°.

In some embodiments, the liquid medium comprises glycerin-based water and structured water.

According to the invention, structured water enhances the molecular activities induced by the biochemical scaffolds of the invention; particularly, molecular activities that modulate Krebs cycle metabolic reactions, processes and/or pathways.

As set forth in priority U.S. application Ser. No. 14/223,392, in some embodiments, the biochemical scaffold comprises a glycerol water solution comprising at least 1200.0 mg/oz. of glycerin.

As indicated above, in some embodiments of the invention, the bioenergetic platforms comprise at least one of the following modulators: a Krebs cycle modulator, glutathione modulator, neurotransmitter modulator, DNA modulator, endocannabinoid modulator or nuclear hormone receptor modulator.

Thus, in some embodiments, the bioenergetic platforms comprise a Krebs cycle modulator and/or glutathione modulator and/or neurotransmitter modulator and/or DNA modulator and/or endocannabinoid modulator and/or nuclear hormone receptor modulator.

In some embodiments, the bioenergetic platforms comprise a plurality of Krebs cycle modulators, and/or glutathione modulators, and/or neurotransmitter modulators, and/or DNA modulators, and/or endocannabinoid modulators and/or nuclear hormone receptor modulators.

As discussed in detail herein, according to the invention, the Krebs cycle modulators induce and/or modulate a Krebs cycle metabolic reaction, process and/or pathway, including, without limitation, Krebs cycle product inhibition and/or substrate availability.

As set forth in FIG. 4A and discussed in detail below, in some embodiments, the Krebs cycle modulators also induce multiple Krebs cycle reactions and/or pathways, resulting in the production of $CO_2$, and/or acetyl-CoA, and/or $FADH_2$, and enhanced adenosine-5'-triphosphate (ATP) energy potential.

As set forth in Applicant's priority U.S. application Ser. Nos. 14/223,392, 16/116,539, 17/732,639, 17/961,836, and 18/400,485, ATP is a multifunctional nucleoside triphosphate that is used as a coenzyme in cells. ATP is one of the end products of photophosphorylation and cellular respiration, and is used by structural proteins in many cellular processes, including biosynthetic reactions, motility, and cell division.

Mammalian mitochondria are organelles that produce more than 90% of cellular ATP. In addition to supplying ATP, i.e., cellular energy, mitochondria are also involved in other cellular mechanisms, including cellular differentiation, apoptosis, as well as cell cycle modulation and cell growth.

Mitochondria provide intracellular ATP via a process called glycolysis, which breaks down monosaccharides into ATP through a series of biochemical processes. Mitochondria contain, among other things, the Krebs cycle enzymes that are involved in heme biosynthesis and the electron transport chain, i.e., the Oxidative Phosphorylation pathway (OxPHOS) system. Due to the large flux of redox reactions necessary to maintain oxidative phosphorylation, mitochondria are the primary site of production of reactive oxygen species (ROS).

As is well established, the OxPHOS system is composed of five (5) large multi-protein enzyme complexes, which collectively transform the reducing energy of NADH and $FADH_2$ to ATP. NADH ubiquinone oxidoreductase (Complex I) contains 45 different subunits, and succinate ubiquinone reductase (Complex II), ubiquinone-cytochrome c oxidoreductase (Complex III), cytochrome c oxidase (Complex IV), and the ATP synthase (Complex V) contain 4, 11, 13 and 16 subunits, respectively.

Four (4) of the OxPHOS enzyme complexes (Complexes I, III, IV and V) have a dual genetic origin, i.e., they are composed of both nuclear DNA-encoded proteins and mitochondrial DNA-encoded proteins.

Transient ischemia (anoxia) results in the local production of extremely high levels of reactive oxygen species (ROS), which can cause long term damage to mitochondria. In the initial phase of transient ischemia, oxygen is scarce, but tissue demands for ATP remain high, resulting in continued functioning of the OxPhos system except for the terminal reduction of oxygen to water by Complex IV. Therefore, reduced electron acceptors "upstream" of Complex IV accumulate to abnormally high levels.

Upon resupply of oxygen, these excess reduced carriers react directly with oxygen to generate highly toxic partially reduced ROS, which are capable of protein, lipid, and DNA modifying reactions. The resulting oxidative damage is deemed to occur mainly inside the mitochondrion, because such ROS are so reactive that they are short lived and cannot diffuse far before finding a target for reaction.

Accordingly, OxPHOS proteins and DNA are deemed the cellular molecules most affected by such oxidative stress. The resulting defects in DNA and OxPHOS proteins can, and in most instances will, result in continued increased production of ROS.

However, it has been found that by modulating the OxPhos system and, thereby, ROS production, which can be achieved by the Krebs cycle modulators of the invention, oxidative stress of cells can be substantially reduced or eliminated.

In a preferred embodiment of the invention, the Krebs cycle modulators of the invention comprise, without limitation, *Schisandra chinensis* berry, epimedium, stinging nettle, yohimbe, red Korean *ginseng*, eleuthero root (or extract), damiana, ashwagandha, maca, L-arginine, L-citrulline, and vitamins $B_1$, $B_2$, $B_3$, $B_5$, $B_7$, $B_9$, and $B_{12}$.

As discussed in detail herein, in a preferred embodiment, the glutathione modulators of the invention induce the generation or proliferation of glutathione and/or a member of the glutathione family, including, without limitation, glutathione peroxidase, and/or catalase synthesis.

In a preferred embodiment, the glutathione modulators of the invention comprise, without limitation, *Schisandra chinensis* berry, epimedium, stinging nettle, yohimbe, red Korean *ginseng*, eleuthero root (or extract), damiana, ashwagandha, maca, iron (Fe), copper (Cu), and vitamins $B_1$, $B_2$, $B_3$, $B_5$, $B_7$, $B_9$, and $B_{12}$.

As also discussed in detail herein, in a preferred embodiment, the neurotransmitter modulators of the invention induce and/or modulate the generation of neurotransmitters and modulate the transmission thereof by and between neurons and, hence, cells.

In a preferred embodiment, the neurotransmitter modulators of the invention comprise, without limitation, valerian root (*Valeriana officinalis* L.), sage (*Salvia officinalis*), epimedium, stinging nettle, maca, eleuthero root, yohimbe, vitamin $B_1$, vitamin $B_6$, vitamin E, and phosphatidylserine.

In some embodiments of the invention, the bioenergetic platforms further comprise a nuclear hormone receptor modulator.

In a preferred embodiment of the invention, the nuclear hormone receptor modulators induce cell receptor activity; preferably, nuclear hormone receptor modulator activity, e.g., the activity of nuclear hormone receptor modulators estrogen receptor-α (ERα), estrogen receptor-β (ERβ), androgen receptor (AR), and mineralocorticoid receptor (MR).

In a preferred embodiment, the nuclear hormone receptor modulators of the invention comprise, without limitation, black cohosh (*Actaea racemosa* L./*Cimicifuga racemosa* (L.) Nutt.), chasteberry (*Vitex agnus-castus* L.), red clover (*Trifolium* pretense L.), primrose (*Oenothera biennis*), fenugreek (*Trigonella foenum-graecum*), dong quai (*Angelica sinensis*), licorice root (*Glycyrrhiza glabra*), and red Korean ginseng (*Panax ginseng*).

As also discussed in detail herein, in a preferred embodiment, the DNA modulators support and/or enhance mitochondrial DNA activity by protecting and/or facilitating the repair of mitochondrial DNA.

In a preferred embodiment, the DNA modulators comprise, without limitation, vitamin $B_{12}$.

In a preferred embodiment of the invention, the endocannabinoid system modulators induce cell receptor and endocannabinoid system activity.

In a preferred embodiment, the endocannabinoid system modulators comprise, without limitation, cannabidiol (CBD) or a component thereof.

Vibrational Energy Platform

As discussed in detail below, in a preferred embodiment of the invention, the vibrational energy platforms of the invention comprise at least one energy signature component derived from at least one biochemical scaffold formulation component, i.e., an herb or biochemical agent.

It has been found, and Applicant has confirmed, that specific, critical frequencies of radiation energy create an interaction by and between a selective herb or biochemical agent and a suitable medium; more particularly, by and between the herb or biochemical agent and electric dipole structures of water molecules in a glycerin-based water, i.e., a glycerol water solution, whereby permanent polarization of the glycerol water molecules, i.e., coherent glycerol water molecules, is generated.

It has also been found and Applicant has also confirmed that water molecules behave as an "active" medium that can capture, replicate, and retain energy signatures of an herb or biochemical agent through defined harmonic oscillation frequencies. Indeed, Applicant has confirmed that highly specific short-range hydrogen bond and electric dipole-to-dipole static interactions between water molecules can be modulated by defined harmonic oscillation frequencies to generate quantum coherent water molecules (also referred to as "energetic blanks"), which form self-assembled coherence domains (CDs) that capture, replicate, and retain energy signatures of herbs and biochemical agents in energy blank regions of the coherence domains.

Figure 5:
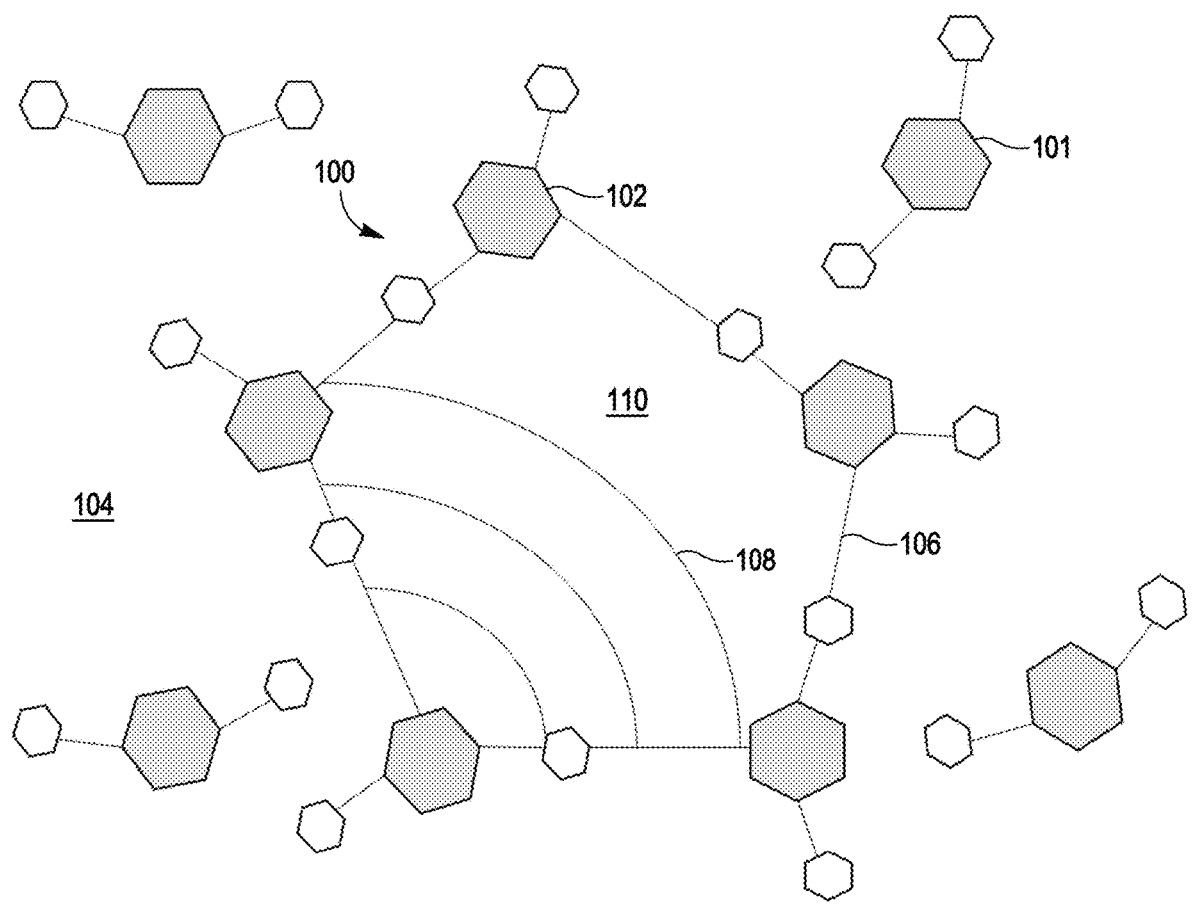
FIG. 5 is a schematic illustration of a coherent domain in a glycerol water solution.

Referring now to FIG. 5, there is shown a coherence domain 100 in a glycerol water solution 104 that comprises a series of quantum coherent water molecules 102, which are bound via short-range hydrogen bonds 106. As illustrated in FIG. 5, the coherence domain 100 comprises an energy signature 108 of a selective herb or biochemical agent that is retained within the energy blank region 110. The coherence domain 100 preferably oscillates in unison with the energy signature 108 retained within the energy blank region 110.

According to the invention, when at least one herb and/or biochemical agent of the invention and a glycerol water solution 104 are subjected to harmonic oscillation at a defined frequency range or sequential harmonic oscillation at defined frequency ranges for a defined, predetermined period of time, the water molecules 101 in the glycerol water solution 104 exhibit quantum coherence, whereby a plurality of distinct quantum coherent water molecules 102 and, hence, coherent domains 100, are generated in the glycerol water solution 104, and, thereby, a unique glycerol water solution (i.e., vibrational energy platform) comprising the following two separate and distinct forms of water molecules is formed: (i) complex, stable quantum coherent water molecules 102, i.e., "energetic blanks," and (ii) water molecules 101.

The quantum coherent water molecules 102 of the glycerol water solution 104, i.e., distinct energetic blanks, form coherent domains 100 that capture, replicate, and retain defined energy signatures 108 of the selective herb and/or biochemical agent of the invention and, hence, chemical components thereof in the energy blank region 110 of the coherence domains 100, i.e., the energy signature 108 of the selective herb and/or biochemical agent is imparted to, captured, replicated, and retained by the coherent domains 100 formed by the quantum coherent water molecules 102 of the glycerol water solution 104.

Applicant has found that when a glycerol water solution comprising coherent domains with a retained energy signature of a selective herb or biochemical agent, i.e., a biochemical scaffold, is delivered to and, hence, is in communication with biological tissue, the biochemical scaffold induces specific biochemical activities through the resonant transfer of the retained energy signatures to the biological tissue and, hence, endogenous cells thereof, whereby a mechanism for the precise regulation of biochemical activities in vivo (based on the properties and function of the transferred energy signature) is provided.

Applicant has thus specifically found that when the biochemical scaffolds of the invention (i) comprise a glycerol-based water solution and defined quantities of black cohosh (*Actaea* racemose L./*Cimicifuga racemosa* (L.) Nutt.), valerian root (*Valeriana officinalis* L.), sage (*Salvia officinalis*), chasteberry (*Vitex agnus-castus* L.), red clover (*Trifolium* pretense L.), primrose (*Oenothera biennis*), fenugreek (*Trigonella foenum-graecum*), dong quai (*Angelica sinensis*), licorice root (*Glycyrrhiza glabra*), and CBD, and (ii) are subjected to a defined harmonic oscillation of the invention (discussed in detail below) and (iii) delivered to a subject, the biochemical scaffolds induce enhanced seminal molecular and cell activity, which substantially reduce the frequency and intensity of hot flashes associated with peri-menopause and menopause.

According to the invention, when the biochemical scaffolds of the invention are also delivered to a subject presenting with non-menopausal hot flashes, such as hot flashes induced by systemic diseases, carcinoid syndrome, systemic mast cell disease, pheochromocytoma, medullary carcinoma of the thyroid, pancreatic islet-cell tumors, renal cell carcinoma, and neurological flushing, the biochemical scaffolds of the invention will also substantially reduce the frequency and intensity of the hot flashes.

According to the invention, the biochemical scaffolds, i.e., liquid compositions thereof, can be subjected to various harmonic oscillations to achieve the above referenced enhanced seminal molecular and cell activity.

In some embodiments, the harmonic oscillation comprises a frequency in the range of approximately 0.0001 kHz to approximately 40000.0 kHz for a period of time in the range of at least 3.0 minutes to 60.0 minutes.

In a preferred embodiment, the harmonic oscillation comprises sequential harmonic oscillation comprising (i) a first frequency in the range of approximately 0.1 kHz to approximately 5.0 kHz for a first period of time in the range of 30.0 seconds to 3.0 minutes, (ii) a second frequency in the range of approximately 10.0 kHz to approximately 50.0 kHz for a second period of time in the range of 30.0 seconds to 3.0 minutes, (iii) a third frequency in the range of approximately 20.0 kHz to approximately 40.0 kHz for a third period of time in the range of 30.0 seconds to 3.0 minutes, (iv) a fourth frequency in the range of approximately 500.0 kHz to approximately 1000.0 kHz for a fourth period of time in the range of 30.0 seconds to 3.0 minutes, and (v) a fifth frequency in the range of approximately 20.0 kHz to approximately 50.0 kHz for a fifth period of time in the range of 30.0 seconds to 3.0 minutes.

In a preferred embodiment, the first, second, third, fourth and fifth periods of time do not collectively extend beyond the range of approximately 5.0 to 7.0 minutes.

In some embodiments, the sequential harmonic oscillation comprises a sixth frequency in the range of approximately 1.0 kHz to approximately 10.0 kHz for a sixth period of time in the range of at least 30.0 seconds to 5.0 minutes.

According to the invention, the harmonic oscillation can also comprise one of the sequential harmonic oscillations disclosed in priority U.S. application Ser. Nos. 14/223,392, 16/116,539, 17/732,639, 17/961,836, and 18/400,485, which are incorporated by reference herein in its entirety.

Applicant has further found that when a glycerol water solution, such as glycerol water solution 104 illustrated in FIG. 5, further comprises structured water, i.e., a glycerol structured water solution, and when at least one herb of the invention and the glycerol structured water solution are subjected to any of the aforementioned harmonic oscillations of the invention, the water molecules in the glycerol structured water solution exhibit enhanced quantum coherence and, thus, form an enhanced plurality of energetic blanks that comprise retained energy signatures of the herb(s).

Applicant has additionally found that when the glycerol structured water solution referenced above is delivered to and, hence, in communication with biological tissue the glycerol structured water solution, i.e., biochemical scaffold, induces enhanced biochemical activity via the resonant transfer of the retained energy signatures to the biological tissue and, hence, endogenous cells thereof.

Bioenergetic Platform

In some embodiments of the invention, the bioenergetic platforms of the invention comprise at least one Krebs cycle modulator, at least one glutathione modulator, at least one neurotransmitter modulator, at least one DNA modulator, at least one endocannabinoid system modulator, or at least one nuclear hormone receptor modulator.

In some embodiments of the invention, the bioenergetic platforms comprise at least one Krebs cycle modulator, at least one glutathione modulator, at least one neurotransmitter modulator, at least one DNA modulator, at least one endocannabinoid system modulator, and at least one nuclear hormone receptor modulator.

As indicated above, in one embodiment of the invention, the bioenergetic platforms comprise a plurality of Krebs cycle modulators, a plurality of neurotransmitter modulators, a glutathione modulator, a DNA modulator, and an endocannabinoid system modulator.

As indicated above and discussed in detail below, according to the invention, the Krebs cycle modulators, glutathione modulators, neurotransmitter modulators, DNA modulators, endocannabinoid system modulators, and nuclear hormone receptor modulators of the invention, alone and particularly, in combination, when delivered to a subject, induce seminal molecular and cell activity, which substantially reduce the frequency and intensity of hot flashes associated with perimenopause and menopause.

Each of the noted modulators is discussed in detail below.

Krebs Cycle Modulators

As indicated above, the Krebs cycle modulators of the invention preferably comprise Schisandra chinensis berry, epimedium, stinging nettle, yohimbe, red Korean ginseng, eleuthero root (or extract), damiana, ashwagandha, maca, L-arginine, L-citrulline, vitamin $B_1$, vitamin $B_2$, vitamin $B_3$, vitamin $B_5$, vitamin $B_7$, vitamin $B_9$, and vitamin $B_{12}$.

As also indicated above, according to the invention, the Krebs cycle modulators of the invention induce and/or modulate at least one Krebs cycle metabolic reaction, process and/or pathway, including, without limitation, Krebs cycle product inhibition and/or substrate availability.

As discussed in detail below, by virtue of the induced Krebs cycle activity, the Krebs cycle modulators of the invention substantially reduce the frequency and intensity of hot flashes associated with perimenopause and menopause.

As set forth in priority U.S. application Ser. Nos. 14/223,392, 16/116,539, 17/732,639, 17/961,836, and 18/400,485, a seminal process associated with the Krebs cycle is the catabolism of carbohydrates, fats, and proteins, which results in the production of a two carbon organic product, i.e., acetate in the form of acetyl-CoA. Acetyl-CoA and two equivalents of water ($H_2O$) are consumed during the Krebs cycle, producing two equivalents of carbon dioxide ($CO_2$) and one equivalent of HS-CoA.

In addition, one complete cycle of the Krebs cycle converts three equivalents of nicotinamide adenine dinucleotide ($NAD^+$) into three equivalents of reduced $NAD^+$ (NADH), one equivalent of ubiquinone (Q) into one equivalent of reduced ubiquinone ($QH_2$), and one equivalent each of guanosine diphosphate (GDP) and inorganic phosphate ($P_i$) into one equivalent of guanosine triphosphate (GTP). The NADH and $QH_2$ generated during the Krebs cycle are in turn used by the oxidative phosphorylation pathway to generate energy-rich adenosine triphosphate (ATP).

A primary source of acetyl-CoA is carbohydrates, which are broken down by glycolysis to produce pyruvate. Pyruvate is decarboxylated by the enzyme pyruvate dehydrogenase to generate acetyl-CoA.

Regulation of the Krebs cycle is largely dependent upon product inhibition and substrate availability. By way of example, NADH, a product of all dehydrogenases in the cycle (with the exception of succinate dehydrogenase) inhibits pyruvate dehydrogenase, isocitrate dehydrogenase, α-ketoglutarate dehydrogenase, and citrate synthase. Acetyl-CoA inhibits pyruvate dehydrogenase, while succinyl-CoA inhibits alpha-ketoglutarate dehydrogenase and citrate synthase.

In a preferred embodiment, the Krebs cycle modulators of the invention also upregulate seminal Krebs cycle components and, thereby, induce enhanced seminal molecular and cell activity, support immune function, which will similarly reduce the frequency and intensity of hot flashes associated with perimenopause and menopause when delivered to a subject.

As indicated above, the Krebs cycle modulators of the invention are also capable of inducing and/or modulating product and/or substrate availability.

By way of example, Applicant has found that eleuthero root facilitates the formation of glucose-6-phosphate, which, as indicated above, converts to pyruvate, which enters the Krebs cycle as Acetyl-CoA and, thereby, facilitates conversion of NAD+ into reduced NAD+ (NADH). The conversion of NAD+ into reduced NAD+ (NADH) and, hence, the provision of an optimal NAD+/NADH ratio induces anti-inflammatory and antioxidant activity in biological tissue that is often associated with menopausal symptoms, including hot flashes. The noted conversion also supports genomic stability, mitochondrial homeostasis, adaptive stress responses, and cell survival.

As set forth in priority U.S. application Ser. Nos. 14/223,392 and 16/116,539, Applicant has also found that maca root works synergistically with eleuthero root by inducing co-factor proliferation, including the co-factor NAD+, which supports activation of the Krebs cycle and, thereby, numerous cell signaling pathways that are associated with symptoms of perimenopause and menopause; particularly, hot flashes.

Maca root also facilitates the production of super oxide dismutase, i.e., an important antioxidant. Intracellular super oxide dismutase converts a highly undesirable reactive oxygen species (ROS) known as superoxide to hydrogen peroxide and oxygen and, thereby, abates oxidative stress generated by superoxide in biological tissue that is similarly associated with symptoms of perimenopause and menopause; particularly, hot flashes.

As is well established, vitamin $B_1$, i.e., thiamine, is involved in RNA and DNA production. Vitamin $B_1$'s active form is a coenzyme called thiamine pyrophosphate (TPP), which converts pyruvate to acetyl Coenzyme A (CoA). Vitamin $B_1$ is also a neuroprotective, site-directed antioxidant that neutralizes ROS proximate to neurons and, hence, protects the neurons, including thermosensitive neurons in the preoptic hypothalamus (POA) that regulate body temperature, from oxidative damage and vasomotor instability resulting therefrom.

Vitamin $B_2$, i.e., riboflavin, is involved in energy production for the electron transport chain and catabolism of fatty acids, i.e., beta oxidation. Vitamin $B_2$ also facilitates the production of endogenous estrogen and, thereby, abates symptoms associated with perimenopause and menopause; particularly, hot flashes, when delivered to a subject presenting with menopausal symptoms.

Vitamin $B_3$, i.e., niacin, is composed of two co-enzyme forms of niacin: nicotinamide adenine dinucleotide (NAD), i.e., an NAD+ precursor, and nicotinamide adenine dinucleotide phosphate (NADP). Vitamin $B_3$ similarly facilitates the production of endogenous estrogens and, thus, similarly abates symptoms associated with perimenopause and menopause; particularly, hot flashes, when delivered to a subject presenting with menopausal symptoms.

Vitamin $B_3$ also abates symptoms associated with perimenopause and menopause; particularly, hot flashes, by ameliorating defects in brain-energy metabolism and oxidative stress associated therewith, which are also often observed in subjects presenting with menopausal symptoms.

Vitamins $B_5$, $B_7$ and $B_9$ also abate symptoms associated with perimenopause and menopause; particularly, hot flashes, by inducing and/or supporting seminal neurometabolic activities; more particularly, inducing and/or supporting seminal neurometabolic activities of thermosensitive neurons in the preoptic hypothalamus (POA) and providing vasomotor stability.

Vitamin $B_5$, i.e., pantothenic acid, is involved in the oxidation of fatty acids and carbohydrates. Coenzyme A, which can be synthesized from Vitamin $B_5$, is involved in the synthesis of several biological components, including amino acids, phospholipids, and neurotransmitters, such as acetylcholine (ACh), which, abate (or significantly reduce the severity of) seminal psychological symptoms associated with menopause, such as the inability to concentrate, depression, memory loss, headache, anxiety, and nervousness.

Vitamin $B_7$, i.e., biotin, also plays a key role in the metabolism of lipids, proteins, and carbohydrates. Vitamin $B_7$ is a critical co-enzyme of four carboxylases: (i) acetyl CoA carboxylase, which is involved in the synthesis of fatty acids from acetate; (ii) propionyl CoA carboxylase, which is involved in gluconeogenesis; (iii) β-methylcrotonyl CoA carboxylase, which is involved in the metabolism of leucin; and (iv) pyruvate CoA carboxylase, which is involved in the metabolism of energy, amino acids, and cholesterol.

Vitamin $B_7$ also regulates and maintains optimal concentrations of glutamate, glutamine, and dopamine, and optimal levels of protein kinase A (PKA) activity in the hippocampus of the brain and, thereby, similarly abates (or significantly reduces the severity of) seminal psychological symptoms of menopause, such as the inability to concentrate, depression, memory loss, headache, anxiety, and nervousness.

Vitamin $B_9$, i.e., folate or folic acid, acts as a co-enzyme in the form of tetrahydrofolate (THF), which is involved in the transfer of single-carbon units in the metabolism of nucleic acids and amino acids. THF is involved in pyrimidine nucleotide synthesis, which is required for normal cell division. Folate also aids in erythropoiesis, i.e., the production of red blood cells.

Further, Vitamin $B_9$ is also a critical component in the synthesis of monoamine neurotransmitters in the brain as a donator of methyl groups to the monoamine neurotransmitters, such as serotonin. Vitamin $B_9$ thus abates symptoms associated with menopause; more particularly, hot flashes, by facilitating increased production of monoamine neurotransmitters in the brain, decreasing noradrenaline levels, and increasing serotonin levels.

Vitamin $B_{12}$, i.e., cobalamin, is a coordination complex of cobalt, which occupies the center of a corrin ligand and is further bound to a benzimidazole ligand and adenosyl group. Vitamin $B_{12}$ induces and/or supports Krebs cycle activity by binding to methylmalonyl-coenzyme A (CoA) mutase and, thereby, mediates the isomerization of methylmalonyl CoA to succinyl CoA.

Vitamin $B_{12}$ also supports nervous system function and, thereby, abates symptoms associated with menopause by facilitating myelinogenesis, i.e., the formation and development of myelin sheath structures, which are critical structures of neurons that insulate the axons of neurons and enable consistent transmission of neurological signals through the axons.

Glutathione Modulators

According to the invention, the glutathione modulators of the invention abate symptoms associated with menopause, including hot flashes, when delivered to a subject presenting with menopause, by inducing several seminal neurometabolic and antioxidant activities.

As indicated above, the glutathione modulators of the invention also comprise one of the aforementioned herbs, i.e., *Schisandra chinensis* berry, epimedium, stinging nettle, yohimbe, red Korean *ginseng*, eleuthero root (or extract), damiana, ashwagandha, maca root, iron (Fe), copper (Cu), and vitamins $B_1$, $B_2$, $B_3$, $B_5$, $B_7$, $B_9$, and $B_{12}$.

As also indicated above, the glutathione modulators of the invention induce (i) the generation or proliferation of glutathione and/or the glutathione family, including, without limitation, glutathione peroxidase, and/or (ii) catalase synthesis.

As also set forth in priority U.S. application Ser. Nos. 14/223,392 and 16/116,539, glutathione; specifically, glutathione peroxidase, is a key intracellular antioxidant that induces conversion of reactive oxygen species (ROS), such as hydrogen peroxide, to $H_2O$ and $O_2$.

As is well established, subjects presenting with menopause often have significantly decreased levels of glutathione reductase activity and, thus, have difficulty maintaining normal endogenous glutathione production levels.

Glutathione reacts directly with ROS in nonenzymatic reactions to lower concentrations of ROS in the body and, thereby, abates symptoms associated with menopause; more particularly, hot flashes, when delivered to a subject presenting with menopause.

Glutathione also lowers concentrations of ROS in the body by serving as an electron donor for the reduction of peroxides in the glutathione peroxidase reaction. In the glutathione peroxidase reaction process, glutathione is converted to its oxidized form, i.e., glutathione disulfide (GSSG), which is also referred to as L-(-)-glutathione. After glutathione is converted to GSSG, the GSSG is reduced back to glutathione by glutathione reductase using reduced nicotinamide adenine dinucleotide phosphate (NADPH) as an electron donor and, hence, regenerates glutathione by transferring electrons from NADPH to GSSG, thus, forming a positive feedback loop that is adapted to continuously remove clinically deleterious ROS from the body and, thereby, similarly abates symptoms associated with menopause; more particularly, hot flashes, when delivered to a subject presenting with menopause.

As additionally set forth in priority U.S. application Ser. Nos. 14/223,392 and 16/116,539, vitamin $B_6$, i.e., pyridoxine, is stored in the body as pyridoxal 5'-phosphate (PLP), which is the co-enzyme form of vitamin $B_6$. Pyridoxine is also involved in the metabolism of amino acids and lipids; in the synthesis of key neurotransmitters, including gamma-aminobutyric acid (GABA) and serotonin, as well as in the production of nicotinic acid (vitamin $B_3$) and hemoglobin. The increased synthesis of GABA abates symptoms associated with menopause; more particularly, hot flashes in subjects presenting with menopause by attenuating hypersensitive thermoregulatory neuronal activity in the preoptic hypothalamus of the brain.

Further, vitamin $B_6$ also induces the production of serotonin and dopamine and, thereby, abates seminal psychological symptoms associated with menopause, such as the inability to concentrate, depression, memory loss, headache, anxiety, and nervousness, when delivered to a subject presenting with menopause.

Neurotransmitter Modulators

Figure 3:
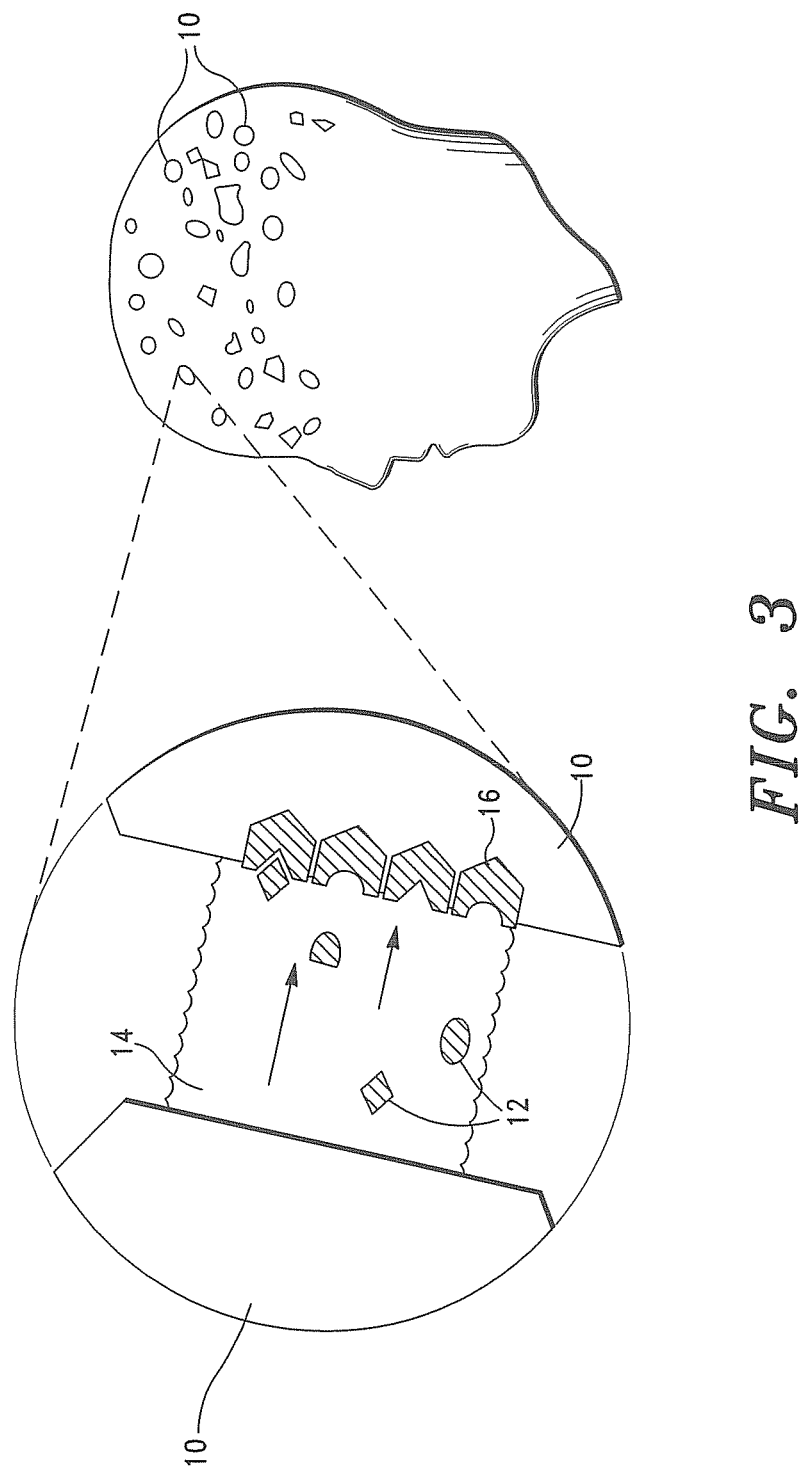
FIG. 3 is a schematic illustration of an electrochemical signal transmission.

It is well established that the human brain contains large numbers of highly specialized cells called neurons. As illustrated in FIG. 3, the neurons 10 connect to and communicate with other neurons and, hence, cells via neurotransmitters 12, i.e., endogenous electrochemical signals, over synapses 14.

As further illustrated in FIG. 3 and discussed in detail below, when a sender neuron 10 generates and transmits neurotransmitters 12, the neurotransmitters 12 activate target receptors 16 on the receiver neuron 10 and, hence, initiate at least one seminal biological activity conducted by receiver neuron 10, such as, in the instance of a hot flash, initiation of systemic vascular dilation that permits increased blood flow through blood vessels and, thereby, rapid elevation of body temperature to uncomfortable levels.

As indicated above, the neurotransmitter modulators of the invention preferably comprise valerian root (*Valeriana officinalis* L.), sage (*Salvia officinalis*), epimedium, stinging nettle, maca root, eleuthero root, ginger root, yohimbe, vitamin $B_1$, vitamin $B_6$, vitamin E, and phosphatidylserine.

As also indicated above, according to the invention, the neurotransmitter modulators of the invention induce (and/or modulate) the generation or proliferation of at least one neurotransmitter, including dopamine, serotonin, and gamma-aminobutyric acid (GABA), and/or the transmission thereof by and between neurons.

According to the invention, the neurotransmitter modulators of the invention similarly abate symptoms associated with menopause; more particularly, hot flashes, when delivered to a subject presenting with menopause, by inducing several seminal neurometabolic activities.

Dopamine, serotonin, and γ-aminobutyric acid (GABA) are key neurotransmitters. Dopamine is a monoamine neurotransmitter that similarly functions as both an inhibitory and excitatory neurotransmitter. As an inhibitory neurotransmitter, dopamine improves balance and general sense of well-being. As an excitatory neurotransmitter, dopamine improves cognition, concentration, and focus. High concentrations of endogenous dopamine also induce vasoconstriction and, thereby, reduce both the frequency and intensity of hot flashes in subjects presenting with menopause by attenuating systemic vascular dilation initiated by the preoptic hypothalamus and restoring vasomotor stability.

Serotonin is another monoamine neurotransmitter that functions as an inhibitory neurotransmitter. Serotonin's biological functions are complex, and modulate numerous psychological functions including mood, cognition, reward, learning, and memory. Serotonin also induces vasoconstriction and, thereby, reduces both the frequency and intensity of hot flashes in subjects presenting with menopause by attenuating systemic vascular dilation initiated by the preoptic hypothalamus and restoring vasomotor stability.

GABA is the most common inhibitory neurotransmitter in the central nervous system of a subject. GABA binds GABA-A and GABA-B receptors on the surfaces of endogenous nervous system cells, e.g., neurons, to attenuate the activity of the endogenous nervous system cells. By virtue of GABA's inhibitory properties, GABA also significantly reduces both the frequency and intensity of hot flashes in subjects presenting with menopause by attenuating hypersensitive thermoregulatory neuronal activity in the preoptic hypothalamus and restoring vasomotor stability.

Applicant has found that valerian root (*Valeriana officinalis* L.) and sage (*Salvia officinalis*) increase the production (and release) of GABA and, thereby, directly reduce both the frequency and intensity of hot flashes in subjects presenting with menopause by attenuating systemic vascular dilation initiated by the preoptic hypothalamus and restoring vasomotor stability.

It has also been found and Applicant has confirmed that valerian root also inhibits the activity of GABA aminotransferases, which are enzymes that breakdown GABA in vivo.

DNA Modulators

According to the invention, the DNA modulator(s) of the invention can comprise various biological or pharmacological agents.

As also indicated above, the DNA modulators of the invention support and/or enhance mitochondrial DNA activity by, among other activities, protecting and/or facilitating the repair of mitochondrial DNA.

According to the invention, the DNA modulators of the invention also abate symptoms associated with menopause; more particularly, hot flashes, when delivered to a subject presenting with menopause, by abating DNA damage and degradation, and protecting and/or facilitating the repair of mitochondrial DNA to achieve optimal cell function and, thereby, physiological functioning.

As is well established and indicated above, mammalian mitochondria are organelles that produce more than 90% of cellular ATP. In addition to supplying ATP, i.e., cellular energy, mitochondria are also involved in other cellular mechanisms, including cellular differentiation, apoptosis, as well as cell cycle modulation and cell growth.

When a cell has temporarily or reversibly stopped dividing or regenerating it is often deemed to have entered a quiescent or senescent state referred to as the G0 phase of the cell cycle.

Non-proliferative cells generally enter the senescent $G_0$ phase or state from the $G_1$ phase and may remain senescent for long periods of time, possibly indefinitely (as is often the case for neurons). Senescence is very common for "adult" cells that are fully differentiated.

The maximum number of cell divisions that a cell can undergo varies from cell type to cell type and organism. In fibroblast cells, this number is about 50 divisions, after which cell division ceases.

However, some cells become senescent after fewer replication cycles due to DNA damage or degradation, e.g., DNA mutations, DNA oxidation, and chromosome losses, which would make a cell's progeny nonviable. If the DNA damage cannot be easily repaired, the cells either prematurely age or self-destruct (i.e., apoptosis or programmed cell death).

The process of cellular senescence can also be triggered by several additional mechanisms, including telomere shortening (i.e., a form of DNA damage or degradation).

Due to DNA replication mechanisms and oxidative stress, telomeres become progressively shorter with each round of replication. As increasing numbers of cell division occur, the telomeres reach a critically short length, which present as double-stranded DNA breaks, resulting in telomere-initiated senescence.

Protecting and/or facilitating the repair of mitochondrial DNA, which can be achieved by virtue of the DNA modulators of the invention, is thus essential to achieve optimal cell function and, thereby, physiological functioning. Healthy mitochondrial DNA also provides healthy enzymatic processes, which are required for oxidative phosphorylation and, hence, continued energy production.

As indicated above, a preferred DNA modulator comprises vitamin $B_{12}$.

According to the invention, vitamin $B_{12}$ supports DNA activity; specifically, DNA synthesis and, in most instances, abates symptoms associated with menopause; more particularly, hot flashes, when delivered to a subject presenting with menopause.

Vitamin $B_{12}$ is involved in the cellular metabolism of carbohydrates, proteins, and lipids. Vitamin $B_{12}$ functions as a co-enzyme in intermediary metabolism for the methionine synthase reaction with methylcobalamin, and the methylmalonyl CoA mutase reaction with adenosylcobalamin.

Vitamin $B_{12}$ also supports nervous system function and, thereby, attenuates hypersensitive thermoregulatory neuronal activity in the preoptic hypothalamus and restores vasomotor stability, by inducing the formation and development of myelin sheath structures, which are critical structures of neurons that insulate the axons of neurons and enable consistent transmission of neurological signals through the axons.

Endocannabinoid System Modulators

According to the invention, the endocannabinoid system modulators of the invention also abate symptoms associated with menopause; more particularly, hot flashes, when delivered to a subject presenting with menopause, by modulating antioxidant activity and reducing inflammation via modulation of transient receptor potential (TRP) channels associated with inflammation.

As indicated above, the endocannabinoid system modulators of the invention induce cell receptor activity; preferably, cannabinoid receptor activity, i.e., receptors CB1 or CB2.

As also indicated above, a preferred endocannabinoid system modulator comprises cannabidiol (CBD).

CBD is one of many cannabinoid molecules produced by plants from the genus *cannabis*, second only to THC in abundance.

CBD activates the two seminal cannabinoid receptors (CB1 and CB2) and, hence, as discussed below, induces several significant physiological activities. One significant physiological activity induced by activating the CB1 and CB2 receptors is modulation of inflammatory activity of tissue and, hence, cells. The inflammation modulation, i.e., reduction thereof, is achieved by (among other factors) modulating TRP channels and, thereby, reactive oxidative stress and reactive oxygen.

As discussed below, in addition to activating the CB1 and CB2 receptors, CBD can, and in many instances will, increase the levels of naturally-produced endocannabinoids, e.g., anandamide and 2-arachidonoyl glycerol (2-AG), by inhibiting the enzymes that break them down.

CBD also activates multiple serotonin receptors in the brain; particularly, serotonin 1A receptors. As a result, CBD can, and often will, induce vasoconstriction and, thereby, reduce the frequency and intensity of hot flashes in subjects presenting with menopause by attenuating systemic vascular dilation initiated by the preoptic hypothalamus and restoring vasomotor stability. CBD can, and often will, also treat psychological menopausal symptoms.

Applicant has also found that CBD is also an effective neurotransmitter modulator. As indicated above, CBD activates the two seminal cannabinoid receptors CB1 and CB2. By activating the CB1 receptors, anandamide is increased and the associated elevation of corticosterone (stress hormone) and 2-arachidonoyl glycerol (2-AG) are reduced, which has a direct effect (and in many instances a calming effect) on the amygdala, i.e., the seminal emotional center of the brain, and, thereby, also abates psychological menopausal symptoms.

Although CBD is a cannabinoid, CBD does not directly interact with and, hence, activates the CB1 and CB2 receptors. Instead, CBD indirectly activates the CB1 and CB2 receptors by modulating signaling through the CB1 and CB2 receptors by inhibiting the enzyme fatty acid amide hydrolase (FAAH). FAAH deactivates anandamide and converts 2-AG to mono acylglycerol. By inhibiting FAAH, more anandamide and 2-AG is available, which further enhances the calming effect on the amygdala.

Nuclear Hormone Receptor Modulators

According to the invention, the nuclear hormone receptor modulators of the invention also abate symptoms associated with menopause; more particularly, hot flashes, when delivered to a subject presenting with menopause.

As indicated above, the nuclear hormone receptor modulators of the invention induce cell receptor activity; preferably, nuclear hormone receptor modulator activity, e.g., the activity of nuclear hormone receptor modulators estrogen receptor-α (ERα), estrogen receptor-β (ERβ), androgen receptor (AR), and mineralocorticoid receptor (MR).

As indicated above, in a preferred embodiment, the nuclear hormone receptor modulators comprise black cohosh (*Actaea racemosa* L./*Cimicifuga racemosa* (L.)

Nutt.), chasteberry (*Vitex agnus-castus* L.), red clover (*Trifolium pretense* L.), primrose (*Oenothera biennis*), fenugreek (*Trigonella foenum-graecum*), licorice root (*Glycyrrhiza glabra*), and dong quai (*Angelica sinensis*).

Applicant has found that black cohosh (*Actaea racemosa* L./*Cimicifuga racemosa* (L.) Nutt.) modulates nuclear hormone receptor activity by inducing a reduction in luteinizing hormone levels and, thereby, abating symptoms associated with menopause; more particularly, hot flashes, when delivered to a subject presenting with menopause.

Applicant has also found that the noted modulation of nuclear hormone receptor activity, e.g., ERα and ERβ activity, by black cohosh also improves the neurometabolic activities of neurons and, thus, similarly abates symptoms associated with menopause; more particularly, hot flashes, when delivered to a subject presenting with menopause.

Applicant has also found that black cohosh further functions as a neurotransmitter modulator by stimulating the production (and release) of dopamine, serotonin, and GABA and, thereby, directly (by targeting the nervous system; more particularly, the preoptic hypothalamus) and indirectly (by targeting the cardiovascular system) reduces both the frequency and intensity of hot flashes in subjects presenting with menopause by attenuating systemic vascular dilation initiated by the preoptic hypothalamus and restoring vasomotor stability.

Black cohosh also functions as a neurotransmitter modulator by acting as a partial agonist of serotonin receptors (also referred to as 5-HT or 5-hydroxytryptamine receptors) to attenuate hypersensitive thermoregulatory neuronal activity in the preoptic hypothalamus.

Applicant has also found that chasteberry (*Vitex agnus-castus* L.) (i) significantly increases ERα gene expression in vivo, and (ii) activates ERα and ERβ, and, thereby, abates symptoms associated with menopause; more particularly, hot flashes, when delivered to a subject presenting with menopause.

Applicant has also found that chasteberry further functions as a neurotransmitter modulator by acting as a partial agonist of dopamine receptors and, thus, activates dopamine receptors to induce vasoconstriction and, thereby, reduce the frequency and intensity of hot flashes in subjects presenting with menopause by attenuating systemic vascular dilation initiated by the preoptic hypothalamus and restoring vasomotor stability.

Applicant has also found that red clover (*Trifolium pretense* L.), licorice root (*Glycyrrhiza glabra*), and dong quai (*Angelica sinensis*) similarly activate ERα and ERβ, and induce a reduction in gonadotropin-releasing hormone, follicle-stimulating hormone, and luteinizing hormone levels and, thereby, similarly abate symptoms associated with menopause; more particularly, hot flashes, when delivered to a subject presenting with menopause.

Applicant has also found that primrose (*Oenothera biennis*) induces the production (and release of) prostaglandin $E_2$ from endogenous cells, which is an anti-inflammatory endocrine factor that effectuates anti-inflammatory activity by downregulating expression of pro-inflammatory cytokines, such as interleukin-1β (IL-1β). By virtue of effectuating anti-inflammatory activity, primrose also abates symptoms associated with menopause; more particularly, hot flashes, when delivered to a subject presenting with menopause.

Applicant has also found that fenugreek (*Trigonella foenum-graecum*) also activates ERα and ERβ and, thereby, provides the following endogenous endocrine activity, including: (i) upregulation of expression of estrogen associated genes, (ii) induction of proliferation of estrogen-dependent endogenous cells, (iii) increase in production of (and secretion of) plasma 17β-estradiol, (iv) an increase in production of (and secretion of) free progesterone, and (v) a decrease in production of (and secretion of) follicle stimulating hormone. By virtue of effectuating the noted endogenous endocrine activity, the fenugreek also abates symptoms associated with menopause; more particularly, hot flashes, when delivered to a subject presenting with menopause.

As also indicated above, another nuclear hormone receptor modulator comprises red Korean *ginseng* (*Panax ginseng*). As is well established, the red Korean *ginseng* comprises a plurality of ginsenosides, including, without limitation, ginsenoside Rb-1, ginsenoside Rg-1, ginsenoside Re, ginsenoside Rg3, ginsenoside Rg5, ginsenoside Rh2, ginsenoside Rh1, ginsenoside Rh3, ginsenoside Rh4, ginsenoside Rs3, ginsenoside Rb-2, ginsenoside Rd, ginsenoside Rp-1, and ginsenoside F4.

As is also well established, ginsenosides (also referred to as "panaxosides") are classified as both steroid glycosides and triterpene saponins. Ginsenosides are derived exclusively from plants belonging to the genus *panax* (i.e., *ginseng*), and exhibit a multitude of biological effects that mimic seminal biological activities of anti-inflammatory steroidal drugs that bind to and activate nuclear hormone receptors. Ginsenosides are thus lipophilic in nature, and by virtue of their steroidal backbone, they can traverse cell membranes of mammalian cells by simple diffusion and regulate cellular functions by binding to specific intracellular target proteins in the cytoplasm and nucleus of the mammalian cells.

It has also been found and Applicant has confirmed that the aforementioned ginsenosides activate seminal nuclear hormone receptors (e.g., ERα, ERβ, AR, and MR) and, hence, as discussed below, induce several significant physiological activities. Such significant physiological activities include the following: (i) ginsenoside Rg3 increases nitric oxide (NO) production by increasing phosphorylation and expression of endothelial NO synthase mediated by ER-dependent PI3-kinase and adenosine monophosphate-activated protein kinase, (ii) ginsenoside-Re activates cardiac potassium channels through a nongenomic pathway through ERα, and the (iii) ginsenosides—Rb1 and Rh1 both activate ERα and estrogen ERβ, which induces activation of estrogen-responsive genes and, thereby, abates symptoms associated with menopause; more particularly, hot flashes, when delivered to a subject presenting with menopause.

Thus, in some embodiments of the invention, the biochemical scaffolds of the invention comprise a liquid composition comprising a liquid medium and at least one of the aforementioned Krebs cycle modulators, neurotransmitter modulators, glutathione modulators, DNA modulators, endocannabinoid system modulators, or nuclear hormone receptor modulators.

In some embodiments of the invention, the biochemical scaffolds of the invention comprise a liquid composition comprising a liquid medium and a Krebs cycle modulator, neurotransmitter modulator, glutathione modulator, DNA modulator, endocannabinoid system modulator, or nuclear hormone receptor modulator.

As indicated above, in one preferred embodiment, the biochemical scaffolds of the invention comprise a liquid composition comprising a liquid medium, a plurality of Krebs cycle modulators, a plurality of neurotransmitter modulators, a plurality of nuclear hormone receptor modulators, a glutathione modulator, a DNA modulator, and an endocannabinoid system modulator.

In a preferred embodiment, the liquid medium comprises glycerin-based water.

In a preferred embodiment, the Krebs cycle modulators comprise vitamin $B_1$, vitamin $B_2$, vitamin $B_3$, vitamin $B_5$ and vitamin $B_9$.

In a preferred embodiment, the neurotransmitter modulators comprise valerian root (*Valeriana officinalis* L.), sage (*Salvia officinalis*), and vitamin $B_6$.

In a preferred embodiment, the nuclear hormone receptor modulators comprise, without limitation, comprise black cohosh (*Actaea racemosa* L./*Cimicifuga racemosa* (L.) Nutt.), chasteberry (*Vitex agnus-castus* L.), red clover (*Trifolium pretense* L.), primrose (*Oenothera biennis*), fenugreek (*Trigonella foenum-graecum*), licorice root (*Glycyrrhiza glabra*), and dong quai (*Angelica sinensis*).

In a preferred embodiment, the glutathione modulator comprises vitamin $B_7$.

In a preferred embodiment, the DNA modulator comprises vitamin $B_{12}$.

In a preferred embodiment, the endocannabinoid system modulator comprises cannabidiol (CBD).

In a preferred embodiment, the liquid medium, i.e., glycerin-based water, comprises in the range of approximately 220 ml to 245 ml.

The preferred quantities of the biochemical scaffold components referenced above are set forth in Table I below.

TABLE I

| Biochemical Scaffold Component | Quantity |
| --- | --- |
| black cohosh (*Actaea racemose* L./*Cimicifuga racemosa* (L.) Nutt.) | approx. 200.0 mg to approx. 750.0 mg |
| valerian root (*Valeriana officinalis* L.) | approx. 200.0 mg to approx. 750.0 mg |
| sage (*Salvia officinalis*) | approx. 200.0 mg to approx. 750.0 mg |
| chasteberry (*Vitex agnus-castus* L.) | approx. 200.0 mg to approx. 750.0 mg |
| red clover (*Trifolium pretense* L.) | approx. 200.0 mg to approx. 750.0 mg |
| primrose (*Oenothera biennis*) | approx. 200.0 mg to approx. 750.0 mg |
| fenugreek (*Trigonella foenum-graecum*) | approx. 200.0 mg to approx. 750.0 mg |
| dong quai (*Angelica sinensis*) | approx. 200.0 mg to approx. 750.0 mg |
| licorice root (*Glycyrrhiza glabra*) | approx. 200.0 mg to approx. 750.0 mg |
| cannabidiol (CBD) | approx. 12.0 mg to approx. 15.0 mg |
| vitamin $B_1$ | approx. 5.0 mg to approx. 7.0 mg |
| vitamin $B_2$ | approx. 0.60 mg to approx. 0.80 mg |
| vitamin $B_3$ | approx. 8.0 mg to approx. 12.0 mg |
| vitamin $B_5$ | approx. 8.0 mg to approx. 12.0 mg |
| vitamin $B_6$ | approx. 1.0 mg to approx. 3.0 mg |
| vitamin $B_7$ | approx. 0.055 mg to approx. 0.065 mg |
| vitamin $B_9$ | approx. 0.155 mg to approx. 0.165 mg |
| vitamin $B_{12}$ | approx. 0.995 mg to approx. 1.005 mg |

As indicated above, in a preferred embodiment of the invention, the biochemical scaffolds of the invention are subjected to harmonic oscillation at a defined frequency or frequencies and a defined period of time or times.

As indicated above, in some embodiments, the harmonic oscillation comprises a frequency in the range of approximately 0.0001 kHz to approximately 40000.0 kHz for a period of time in the range of at least 3.0 minutes to 60.0 minutes.

According to the invention, the harmonic oscillation can also comprise multiple concomitant harmonic oscillation frequencies and multiple sequential harmonic oscillation frequencies.

Indeed, in a preferred embodiment, the harmonic oscillation comprises sequential harmonic oscillation comprising (i) a first frequency in the range of approximately 0.1 kHz to approximately 5.0 kHz for a first period of time in the range of 30.0 seconds to 3.0 minutes, (ii) a second frequency in the range of approximately 10.0 kHz to approximately 50.0 kHz for a second period of time in the range of 30.0 seconds to 3.0 minutes, (iii) a third frequency in the range of approximately 20.0 kHz to approximately 40.0 kHz for a third period of time in the range of 30.0 seconds to 3.0 minutes, (iv) a fourth frequency in the range of approximately 500.0 kHz to approximately 1000.0 kHz for a fourth period of time in the range of 30.0 seconds to 3.0 minutes, and (v) a fifth frequency in the range of approximately 20.0 kHz to approximately 50.0 kHz for a fifth period of time in the range of 30.0 seconds to 3.0 minutes.

In a preferred embodiment, the first, second, third, fourth and fifth periods of time do not collectively extend beyond the range of approximately 5.0 minutes to 7.0 minutes.

In some embodiments, the sequential harmonic oscillation comprises a sixth frequency in the range of approximately 1.0 kHz to approximately 10.0 kHz for a sixth period of time in the range of at least 30.0 seconds to 5.0 minutes.

According to the invention, there are thus provided biochemical scaffolds for treating, i.e. abating, symptoms associated with menopause; particularly, hot flashes, when delivered to a subject presenting with menopause.

In one embodiment of the invention, the biochemical scaffold comprises a liquid composition comprising glycerin-based water, black cohosh (*Actaea* racemose L./*Cimicifuga racemosa* (L.) Nutt.), valerian root (*Valeriana officinalis* L.), sage (*Salvia officinalis*), chasteberry (*Vitex agnus-castus* L.), red clover (*Trifolium pretense* L.), primrose (*Oenothera biennis*), fenugreek (*Trigonella foenum-graecum*), dong quai (*Angelica sinensis*), licorice root (*Glycyrrhiza glabra*), and cannabidiol (CBD), which is subjected to the preferred harmonic oscillation of the invention described above.

In another embodiment of the invention, the biochemical scaffold comprises a liquid composition comprising glycerin-based water, black cohosh (*Actaea* racemose L./*Cimicifuga racemosa* (L.) Nutt.), valerian root (*Valeriana officinalis* L.), sage (*Salvia officinalis*), chasteberry (*Vitex agnus-castus* L.), red clover (*Trifolium pretense* L.), primrose (*Oenothera biennis*), fenugreek (*Trigonella foenum-graecum*), dong quai (*Angelica sinensis*), licorice root (*Glycyrrhiza glabra*), cannabidiol (CBD), vitamin $B_1$, vitamin $B_2$, vitamin $B_3$, vitamin $B_5$, vitamin $B_6$, vitamin $B_7$, vitamin $B_9$, and vitamin $B_{12}$, which is similarly subjected to the preferred harmonic oscillation of the invention described above.

According to the invention, there are thus also provided methods for treating, i.e. abating, menopausal symptoms of a subject; particularly, hot flashes. In one embodiment, the method comprises:

(i) providing a biochemical scaffold comprising a liquid composition comprising glycerin-based water, black cohosh (*Actaea* racemose L./*Cimicifuga racemosa* (L.) Nutt.), valerian root (*Valeriana officinalis* L.), sage (*Salvia officinalis*), chasteberry (*Vitex agnus-castus* L.), red clover (*Trifolium* pretense L.), primrose (*Oenothera biennis*), fenugreek (*Trigonella foenum-graecum*), dong quai (*Angelica sinensis*), licorice root (*Glycyrrhiza glabra*), and cannabidiol (CBD);

(ii) subjecting the biochemical scaffold to harmonic oscillation at a frequency in the range of approximately 0.0001 kHz to approximately 40000.0 kHz for a period of time in the range of at least 3.0 minutes to 60.0 minutes; and (iii) delivering a therapeutically effective amount of the biochemical scaffold to the subject.

In some embodiments, the biochemical scaffold further comprises vitamin $B_1$, vitamin $B_2$, vitamin $B_3$, vitamin $B_5$, vitamin $B_6$, vitamin $B_7$, vitamin $B_9$, and vitamin $B_{12}$.

In another embodiment, the method for treating menopausal symptoms of a subject comprises:
  (i) providing a biochemical scaffold comprising a liquid composition comprising glycerin-based water, black cohosh (*Actaea racemose* L./*Cimicifuga racemosa* (L.) Nutt.), valerian root (*Valeriana officinalis* L.), sage (*Salvia officinalis*), chasteberry (*Vitex agnus-castus* L.), red clover (*Trifolium* pretense L.), primrose (*Oenothera biennis*), fenugreek (*Trigonella foenum-graecum*), dong quai (*Angelica sinensis*), licorice root (*Glycyrrhiza glabra*), and cannabidiol (CBD);
  (ii) subjecting the biochemical scaffold to sequential harmonic oscillation at (i) a first frequency in the range of approximately 0.1 kHz to approximately 5.0 kHz for a first period of time in the range of 30.0 seconds to 3.0 minutes, (ii) a second frequency in the range of approximately 10.0 kHz to approximately 50.0 kHz for a second period of time in the range of 30.0 seconds to 3.0 minutes, (iii) a third frequency in the range of approximately 20.0 kHz to approximately 40.0 kHz for a third period of time in the range of 30.0 seconds to 3.0 minutes, (iv) a fourth frequency in the range of approximately 500.0 kHz to approximately 1000.0 kHz for a fourth period of time in the range of 30.0 seconds to 3.0 minutes, and (v) a fifth frequency in the range of approximately 20.0 kHz to approximately 50.0 kHz for a fifth period of time in the range of 30.0 seconds to 3.0 minutes; and
  (iii) delivering a therapeutically effective amount of the biochemical scaffold to the subject.

In some embodiments, the biochemical scaffold similarly further comprises vitamin $B_1$, vitamin $B_2$, vitamin $B_3$, vitamin $B_5$, vitamin $B_6$, vitamin $B_7$, vitamin $B_9$, and vitamin $B_{12}$.

As set forth in priority U.S. application Ser. No. 14/223,392, the biochemical scaffolds of the invention can be delivered to host tissue by various conventional means, including, without limitation, oral, sublingual, nasal, direct injection, topical application, etc.

As will readily be appreciated by one having ordinary skill in the art, the present invention provides numerous advantages compared to prior art formulations and methods for treating, i.e. abating, menopausal symptoms of a subject; particularly, hot flashes. Among the advantages are the following:

The provision of biochemical scaffolds and methods associated therewith, which substantially abate the frequency and intensity of hot flashes associated with perimenopause and menopause without the side effects and health risks associated with hormonal and non-hormonal compositions and methods.

The provision of biochemical scaffolds and methods associated therewith that substantially abate the frequency and intensity of hot flashes associated with perimenopause and menopause by inducing and/or modulating a plurality of seminal molecular and cell activities.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A method of treating menopausal symptoms of a subject, comprising the steps of:
  (i) providing a liquid composition comprising glycerin-based water, black cohosh in the range of from about 200.0 mg to about 750.0 mg, valerian root in the range of from about 200.0 mg to about 750.0 mg, sage in the range of from about 200.0 mg to about 750.0 mg, chasteberry in the range of from about 200.0 mg to about 750.0 mg, red clover in the range of from about 200.0 mg to about 750.0 mg, primrose in the range of from about 200.0 mg to about 750.0 mg, fenugreek in the range of from about 200.0 mg to about 750.0 mg, dong quai in the range of from about 200.0 mg to about 750.0 mg, licorice root in the range of from about 200.0 mg to about 750.0 mg, and cannabidiol in the range of from about 12.0 mg to about 15.0 mg;
  (ii) subjecting said liquid composition to harmonic oscillation at a frequency in the range of 0.0001 kHz to 40000.0 kHz for a period of time in the range of 3.0 minutes to 60.0 minutes; and
  (iii) delivering a therapeutically effective amount of said liquid composition to said subject.

2. The method of claim 1, wherein said liquid composition further comprises vitamin $B_1$ in the range of from about 5.0 mg to about 7.0 mg, vitamin $B_2$ in the range of from about 0.60 mg to about 0.80 mg, vitamin $B_3$ in the range of from about 8.0 mg to about 12.0 mg, vitamin $B_5$ in the range of from about 8.0 mg to about 12.0 mg, vitamin $B_6$ in the range of from about 1.0 mg to about 3.0 mg, vitamin $B_7$ in the range of from about 0.055 mg to about 0.065 mg, vitamin $B_9$ in the range of from about 0.155 mg to about 0.165 mg, and vitamin $B_{12}$ in the range of from about 0.995 mg to about 1.005 mg.

3. A method of treating menopausal symptoms of a subject, comprising the steps of:
  (i) providing a liquid composition comprising glycerin-based water, black cohosh in the range of from about 200.0 mg to about 750.0 mg, valerian root in the range of from about 200.0 mg to about 750.0 mg, sage in the range of from about 200.0 mg to about 750.0 mg, chasteberry in the range of from about 200.0 mg to about 750.0 mg, red clover in the range of from about 200.0 mg to about 750.0 mg, primrose in the range of from about 200.0 mg to about 750.0 mg, fenugreek in the range of from about 200.0 mg to about 750.0 mg, dong quai in the range of from about 200.0 mg to about 750.0 mg, licorice root in the range of from about 200.0 mg to about 750.0 mg, and cannabidiol in the range of from about 12.0 mg to about 15.0 mg;
  (ii) subjecting said liquid composition to sequential harmonic oscillation at a first frequency in the range of approximately 0.1 kHz to approximately 5.0 kHz for a first period of time in the range of 30.0 seconds to 3.0 minutes, a second frequency in the range of approximately 10.0 kHz to approximately 50.0 kHz for a second period of time in the range of 30.0 seconds to 3.0 minutes, a third frequency in the range of approximately 20.0 kHz to approximately 40.0 kHz for a third period of time in the range of 30.0 seconds to 3.0 minutes, a fourth frequency in the range of approximately 500.0 kHz to approximately 1000.0 kHz for a fourth period of time in the range of 30.0 seconds to 3.0 minutes, and a fifth frequency in the range of approximately 20.0 kHz to approximately 50.0 kHz for a fifth period of time in the range of 30.0 seconds to 3.0 minutes; and (iii) delivering a therapeutically effective amount of said liquid composition to said subject.

4. The method of claim 3, wherein said sequential harmonic oscillation does not exceed a total harmonic oscillation period of time of 5.0 minutes.

5. The method of claim 3, wherein said liquid composition further comprises vitamin $B_1$ in the range of from about 5.0 mg to about 7.0 mg, vitamin $B_2$ in the range of from about 0.60 mg to about 0.80 mg, vitamin $B_3$ in the range of from about 8.0 mg to about 12.0 mg, vitamin $B_5$ in the range of from about 8.0 mg to about 12.0 mg, vitamin $B_6$ in the range of from about 1.0 mg to about 3.0 mg, vitamin $B_7$ in the range of from about 0.055 mg to about 0.065 mg, vitamin $B_9$ in the range of from about 0.155 mg to about 0.165 mg, and vitamin $B_{12}$ in the range of from about 0.995 mg to about 1.005 mg.

\* \* \* \* \*